US012663573B2

(12) United States Patent
Tachibana et al.

(10) Patent No.: US 12,663,573 B2
(45) Date of Patent: Jun. 23, 2026

(54) PERIPHERAL SURFACE-EMITTING LINEAR LIGHT GUIDE AND METHOD FOR MANUFACTURING THE SAME

(71) Applicant: Proterial, Ltd., Tokyo (JP)

(72) Inventors: Kota Tachibana, Tokyo (JP); Ryuta Takahashi, Tokyo (JP); Seiji Kojima, Tokyo (JP)

(73) Assignee: Proterial, Ltd., Tokyo (JP)

( * ) Notice: Subject to any disclaimer, the term of this patent is extended or adjusted under 35 U.S.C. 154(b) by 175 days.

(21) Appl. No.: 18/384,669

(22) Filed: Oct. 27, 2023

(65) Prior Publication Data

US 2024/0176057 A1 May 30, 2024

(30) Foreign Application Priority Data

Nov. 25, 2022 (JP) ................................. 2022-188340

(51) Int. Cl.
*A61N 5/06* (2006.01)
*A61B 1/07* (2006.01)
(Continued)

(52) U.S. Cl.
CPC ................ *G02B 6/001* (2013.01); *A61B 1/07* (2013.01); *A61B 18/22* (2013.01); *A61B 18/24* (2013.01);
(Continued)

(58) Field of Classification Search
CPC ............ A61B 2018/2261; A61B 18/22; A61N 2005/063; G02B 6/262; G02B 6/241; G02B 6/001; G02B 6/0008; G02B 6/3624
See application file for complete search history.

(56) References Cited

U.S. PATENT DOCUMENTS 5,373,571 A * 12/1994 Reid ...................... A61B 18/22
                                                                       385/128
5,429,635 A * 7/1995 Purcell, Jr. ............. A61N 5/062
                                                                       606/1
(Continued)

FOREIGN PATENT DOCUMENTS

EP            3185057 A1 * 6/2017 ............... G02B 6/26
GB            2154761 A * 9/1985 .......... G02B 6/4203
(Continued)

OTHER PUBLICATIONS

Refractive index.info, Refractive index database, Fused silica (fused quartz), https://refractiveindex.info/?shelf=glass&book=fused_silica &page=Malitson, accessed Sep. 10, 2025 (Year: 2025).*
(Continued)

*Primary Examiner* — Michelle R Connelly
(74) *Attorney, Agent, or Firm* — McGinn IP Law Group, PLLC

(57) ABSTRACT

A peripheral surface-emitting linear light guide is provided with an optical fiber including a core, an outer peripheral surface of which is exposed from a cladding at one end in a longitudinal direction, and a light-scattering member that covers an entire periphery of the outer peripheral surface of the core in an exposed portion over a predetermined axial length range. The light emitted from the outer peripheral surface of the core is scattered and radiated by the light-scattering member. The light-scattering member includes a light transmissive base material having a higher refractive index than the core and light-scattering particles that scatter the light incident on the base material, and the light-scattering particles are dispersed and mixed in a certain proportion throughout the base material. At least a portion of the light-scattering member in the longitudinal direction is
(Continued)

an incremental portion whose thickness increases gradually toward a tip side of the core.

19 Claims, 9 Drawing Sheets

(51) Int. Cl.

| | |
|---|---|
| *A61B 18/22* | (2006.01) |
| *A61B 18/24* | (2006.01) |
| *F21V 8/00* | (2006.01) |

(52) U.S. Cl.
CPC .... *A61N 5/0601* (2013.01); *A61B 2018/2244* (2013.01); *A61B 2018/2261* (2013.01); *A61N 2005/0602* (2013.01); *A61N 2005/063* (2013.01)

(56) References Cited

U.S. PATENT DOCUMENTS

| | | | | | |
|---|---|---|---|---|---|
| 5,530,780 | A | * | 6/1996 | Ohsawa | G02B 6/3624 |
| | | | | | 385/901 |
| 5,671,314 | A | * | 9/1997 | Gregory | A61N 5/0601 |
| | | | | | 385/127 |
| 5,695,583 | A | * | 12/1997 | van den Bergh | G02B 6/0008 |
| | | | | | 427/407.1 |
| 5,976,175 | A | * | 11/1999 | Hirano | A61N 5/0601 |
| | | | | | 606/2 |
| 6,810,184 | B2 | * | 10/2004 | Skutnik | G02B 6/02 |
| | | | | | 385/124 |
| 7,412,141 | B2 | * | 8/2008 | Gowda | G02B 6/241 |
| | | | | | 385/139 |
| 7,991,260 | B2 | * | 8/2011 | Doody | G02B 6/4296 |
| | | | | | 385/139 |
| 9,345,543 | B2 | * | 5/2016 | Brown | A61B 18/24 |
| 9,931,165 | B2 | * | 4/2018 | Mayer | A61B 18/20 |
| 10,543,042 | B2 | * | 1/2020 | Wu | G02B 6/262 |
| 11,693,177 | B2 | * | 7/2023 | Tamura | A61N 5/0601 |
| | | | | | 385/147 |
| 11,786,305 | B2 | * | 10/2023 | Suzuki | A61M 25/10 |
| | | | | | 606/15 |
| 12,007,096 | B2 | * | 6/2024 | Schultheis | G02B 6/001 |
| 12,150,705 | B2 | * | 11/2024 | Stein | A61B 18/22 |
| 12,242,097 | B2 | * | 3/2025 | Kang | A61N 5/062 |
| 2005/0137587 | A1 | * | 6/2005 | Nield | A61B 18/22 |
| | | | | | 606/15 |
| 2007/0179488 | A1 | * | 8/2007 | Trusty | A61B 18/22 |
| | | | | | 606/16 |
| 2008/0154317 | A1 | * | 6/2008 | Loebel | A61B 18/22 |
| | | | | | 607/2 |
| 2015/0037203 | A1 | | 2/2015 | Pan | |
| 2019/0275346 | A1 | * | 9/2019 | Maeda | A61N 5/0603 |
| 2022/0317366 | A1 | | 10/2022 | Tamura | |
| 2023/0087914 | A1 | * | 3/2023 | Schultheis | G02B 6/3624 |
| | | | | | 362/257 |

FOREIGN PATENT DOCUMENTS

| | | | |
|---|---|---|---|
| JP | 2015-510668 | A | 4/2015 |
| JP | 2022-158714 | A | 10/2022 |

OTHER PUBLICATIONS

EPO-TEK® 301-1 Technical Data Sheet, Epoxy Technology, https://www.epotek.com/docs/en/Datasheet/301-1.pdf, Revision VII, Jun. 2021 (Year: 2021).*

Japanese Office Action dated Dec. 2, 2025 in Japanese Patent Application No. 2022-188340 with machine English translation.

* cited by examiner

PERIPHERAL SURFACE-EMITTING LINEAR LIGHT GUIDE AND METHOD FOR MANUFACTURING THE SAME

CROSS-REFERENCE TO RELATED APPLICATIONS

The present application is based on Japanese patent application No. 2022-188340 filed on Nov. 25, 2022, the entire contents of which are incorporated herein by reference.

TECHNICAL FIELD

The present invention relates to a peripheral surface-emitting linear light guide with an optical fiber and a light-scattering member, and a method for manufacturing the same.

BACKGROUND OF THE INVENTION

Conventionally, e.g., catheter treatment is performed by inserting an optical fiber catheter equipped with an optical fiber into a luminal organ such as the esophagus or intestine of the human body, or into a blood vessel or heart of the human body, and treating the affected site with light emitted from the core of the optical fiber. The applicant has proposed a peripheral surface-emitting linear light guide for such catheter therapy, as described in Patent Literature 1.

The peripheral surface-emitting linear light guide described in Patent Literature 1 has an optical fiber including a cladding that is removed to expose a core, and a light-scattering member in which light-scattering particles are dispersedly mixed into a light-transmissive base material having a higher refractive index than the core, and an outer peripheral surface of the exposed core is covered by the light-scattering member. The light-scattering member consists of a plurality of layers with different mixing ratios of light-scattering particles to the base material to enhance the homogeneity of light intensity in the axial direction, and the plurality of layers overlap at least partially in the radial direction of the core. In forming this light-scattering member, multiple types of liquids with different mixing ratios of light-scattering particles are prepared, and the step of adhering these liquids to the outer periphery of the core and curing them is repeated.

CITATION LIST

Patent Literature 1: JP2022-158714A

SUMMARY OF THE INVENTION

Optical fiber catheters used for catheter treatment (i.e., catheterization) are disposable, and there is a need to reduce the cost of catheters. The outer peripheral surface-emitting linear light guide configured as described above required many man-hours and long processing time to form a light-scattering member having multiple layers with different mixing ratios of light-scattering particles, making it difficult to reduce the cost.

Therefore, it is an object of the present invention to provide a peripheral surface-emitting linear light guide with a configuration that enables cost reduction while increasing the homogeneity of light intensity, and a method for manufacturing the peripheral surface-emitting linear light guide.

For the purpose of solving the above problem, one aspect of the present invention provides a peripheral surface-emitting linear light guide, comprising:

an optical fiber including a core, an outer peripheral surface of which is exposed from a cladding at one end in a longitudinal direction; and a light-scattering member that covers an entire periphery of the outer peripheral surface of the core in an exposed portion over a predetermined axial length range, wherein light emitted from the outer peripheral surface of the core is scattered and radiated by the light-scattering member, wherein the light-scattering member comprises a light transmissive base material having a higher refractive index than the core and light-scattering particles that scatter the light incident on the base material, and the light-scattering particles are dispersed and mixed in a certain proportion throughout the base material, and wherein at least a portion of the light-scattering member in the longitudinal direction is an incremental portion whose thickness increases gradually toward a tip side of the core.

Further, for the purpose of solving the above problem, another aspect of the present invention provides a method for manufacturing the peripheral surface-emitting linear light guide as described above, comprising:

processing the optical fiber to expose the outer peripheral surface of the core from the cladding;

preparing a liquid to be used as the light-scattering member;

immersing the exposed core in the liquid;

pulling-up the core from the liquid by moving the core and the liquid relative to each other in a vertical direction; and curing the liquid adhered to the core, wherein, in the pulling-up step, when forming the incremental portion of the light-scattering member, a pulling-up speed is varied to gradually increase a thickness of the liquid adhering to the outer peripheral surface of the core.

Advantageous Effects of the Invention

According to the outer peripheral surface-emitting linear light guide and the manufacturing method thereof according to the present invention, it is possible to reduce costs while increasing the homogeneity of light intensity.

BRIEF DESCRIPTION OF DRAWINGS

FIGS. 4A and 4B are cross-sectional views of the outer peripheral surface-emitting linear light guide in a cross-section perpendicular to a central axis of the core, in which FIG. 4A shows a cross-section of a small diameter end of an incremental portion of the light-scattering member, and FIG. 4B shows a cross-section of a large diameter end of the incremental portion of the light-scattering member.

DETAILED DESCRIPTION OF THE INVENTION

Embodiment

Figure 1:
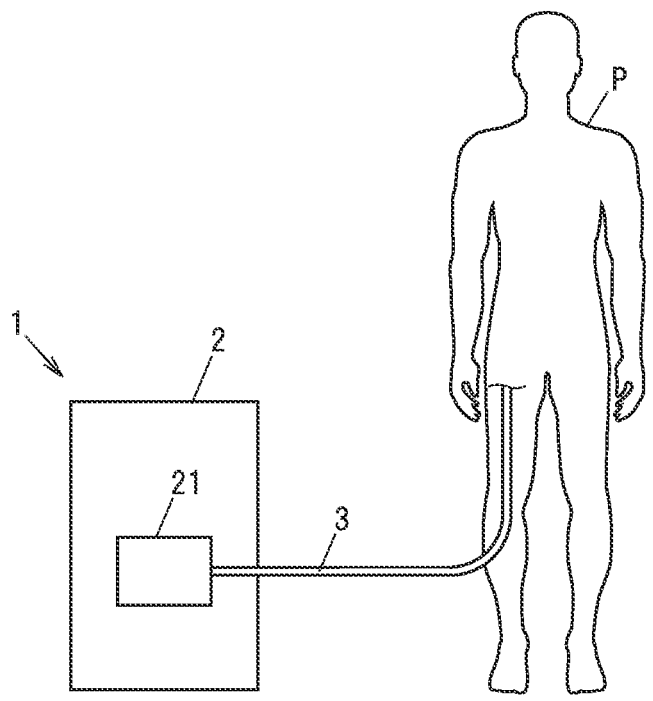
FIG. 1 is a schematic diagram showing a treatment device with a catheter including a peripheral surface-emitting linear light guide according to an embodiment of the present invention, together with a patient to be treated.

FIG. 1 is a schematic diagram showing a treatment device using a peripheral surface-emitting linear light guide according to an embodiment of the present invention as a catheter, together with a patient to be treated. The treatment device 1 includes a main body 2, and a peripheral surface-emitting linear light guide 3, in which a tip of the peripheral surface-emitting linear light guide 3 is inserted into the body of patient P. The main body 2 includes a light source 21 that emits laser light, and the laser light emitted by the light source 21 enters a base end (i.e., proximal end) of the peripheral surface-emitting linear light guide 3.

Configuration of the Outer Peripheral Surface-Emitting Linear Light Guide

Figure 2:
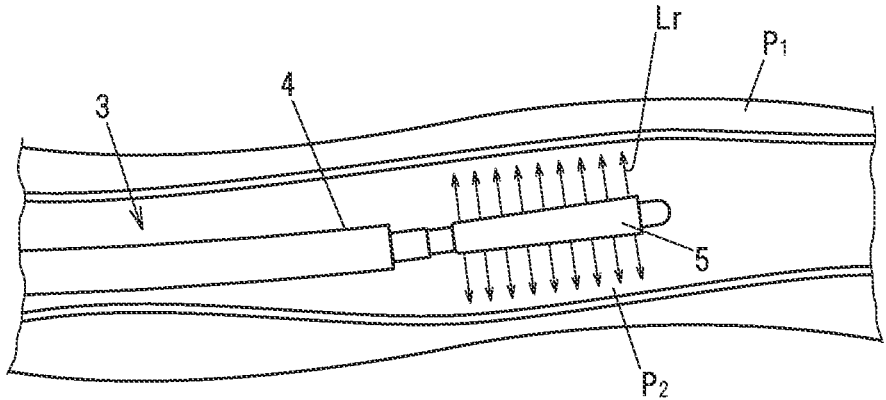
FIG. 2 is a schematic diagram showing a tip portion of the catheter inserted into the patient's body.

FIG. 2 is a schematic diagram showing an end portion of the peripheral surface-emitting linear light guide 3 inserted into the body of patient P. In FIG. 2, a portion of patient P's blood vessel $P_1$ is cut out to show the end portion of the peripheral surface-emitting linear light guide 3 inserted into blood vessel $P_1$. The laser light Lr scattered and emitted from the peripheral surface-emitting linear light guide 3 irradiates the treatment site $P_2$ and reacts with the drug previously contained in the treatment site $P_2$. This results in intravascular laser therapy.

Figure 3A:
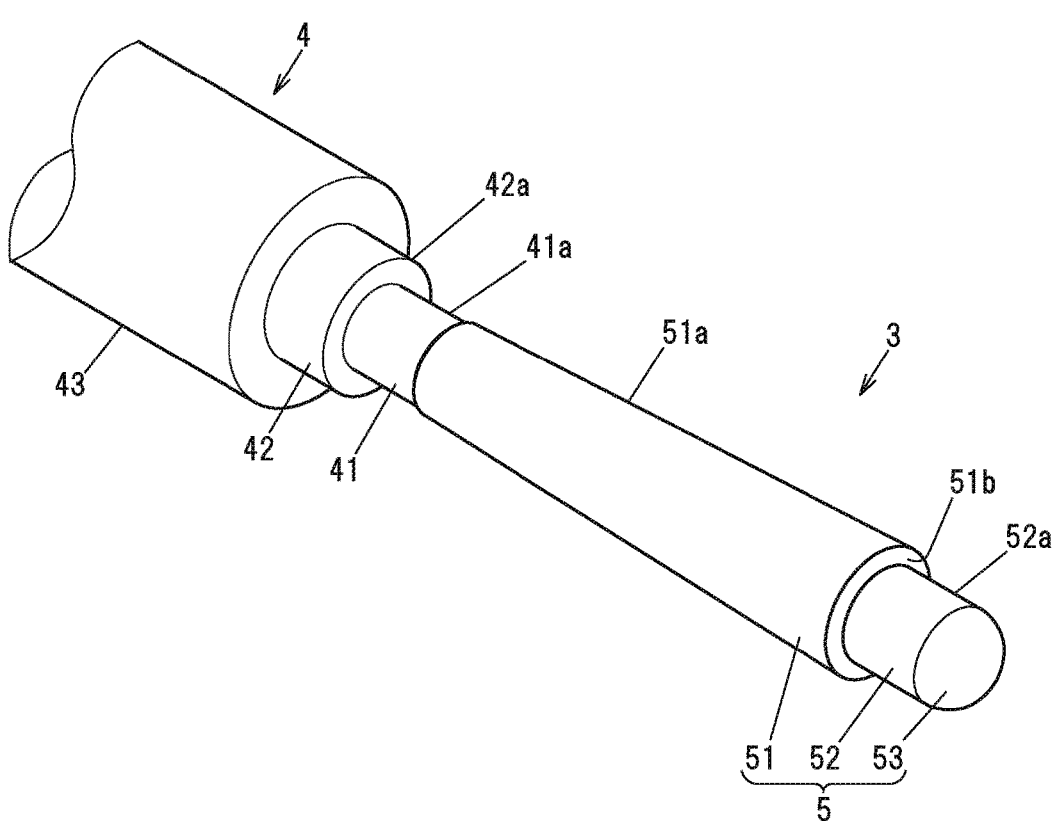
FIG. 3A is a perspective view of one end of the outer peripheral surface-emitting linear light guide.
Figure 3B:
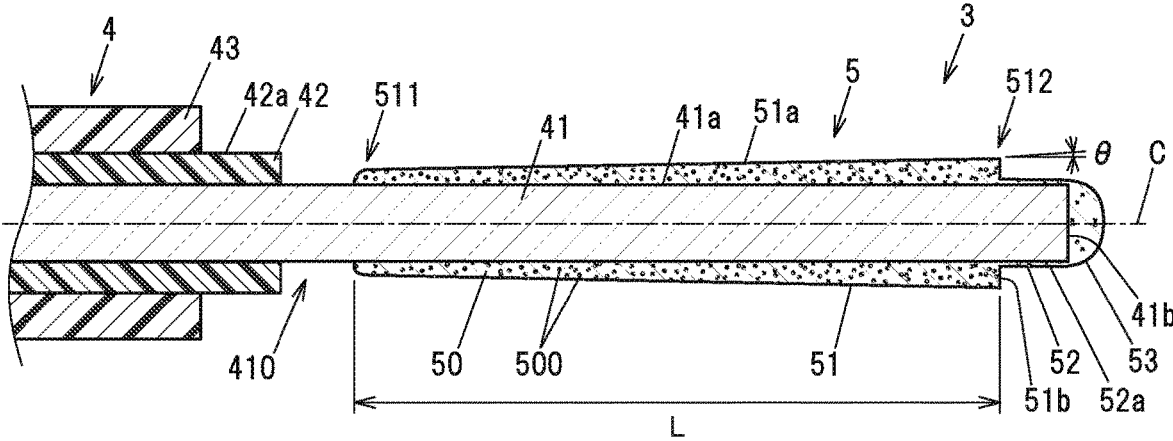
FIG. 3B is a cross-sectional view along an axial direction of the outer peripheral surface-emitting linear light guide.

FIG. 3A is a perspective view of one end of the peripheral surface-emitting linear light guide 3. FIG. 3B is a cross-sectional view of the peripheral surface-emitting linear light guide 3 along the axial direction. The peripheral surface-emitting linear light guide 3 includes an optical fiber 4 that guides the laser light emitted by the light source 21 to the treatment site $P_2$, and a light-scattering member 5 provided at one end of the optical fiber 4. The optical fiber 4 includes a core 41, a cladding 42, and a sheath 43. At one end of the optical fiber 4 in the longitudinal direction, an outer peripheral surface 42a of the cladding 42 is exposed from the sheath 43, and an outer peripheral surface 41a of the core 41 is also exposed from the cladding 42. In FIGS. 3A and 3B, the thickness of the light-scattering member 5 is exaggerated for clarity of explanation.

The light-scattering member 5 covers the entire outer peripheral surface 41a of the core 41 in the portion exposed from the cladding 42 over a predetermined axial length range. The axial length of the core 41 in the portion covered by the light-scattering member 5 is, e.g., 3 to 7 cm. A longitudinal portion of the core 41 is an uncovering portion 410 that is not covered by either the cladding 42 or the light-scattering member 5.

The optical fiber 4 in the present embodiment is a quartz glass optical fiber in which the core 41 is made of quartz glass and the cladding 42 is made of polymer. The sheath 43 is made of fluoropolymer, more specifically, ETFE (ethylene tetrafluoroethylene copolymer). The diameter of the core 41 is, e.g., 200 µm. The refractive index of the core 41 is higher than that of the cladding 42, and light propagating in the core 41 in the cladding 42 is totally reflected off the interface with the cladding 42.

The light-scattering member 5 scatters and radiates the light emitted from the outer peripheral surface 41a of the core 41. The light-scattering member 5 includes a light transmissive base material 50 having a higher refractive index than the core 41, and a number of light-scattering particles 500 that scatter the light incident on the base material 50, and the light-scattering particles 500 are dispersed and mixed in a certain proportion throughout the base material 50. Here, dispersion-mixed at a constant ratio means that the light-scattering particles 500 are mixed so that the light-scattering particles 500 are evenly dispersed throughout the base material 50 so that the distribution of the light-scattering particles 500 is not biased to a part within the base material 50. In the present embodiment, the base material 50 is a thermosetting resin. The light-scattering particles 500 are so fine that they cannot be recognized by the naked eye, but the size of the light-scattering particles 500 is exaggerated in FIG. 3B.

The base material 50 has a higher refractive index than the core 41, and light emitted from the outer peripheral surface 41a of the core 41 enters the light-scattering member 5. In this embodiment, the base material 50 is silicone resin and its refractive index is, e.g., 1.52. The refractive index of the core 41 is, e.g., 1.46. The light-scattering particles 500 are metal particles that reflect light incident on the light-scattering member 5. In this embodiment, titanium oxide ($TiO_2$) is used as the light-scattering particles 500. However, the present invention is not limited thereto, and fine powders of aluminum oxide (alumina), or fine metallic powders of silver, copper, iron, or alloys thereof may also be used as the light-scattering particles 500.

The light-scattering member 5 has an incremental portion 51 whose thickness gradually increases toward a tip side (i.e., distal end side) of the core 41, an annular thin-walled portion 52 provided on the tip side of the core 41 relative to the incremental portion 51, and a tip-covering portion 53 provided around the tip surface 41b of the core 41. The annular thin-walled portion 52 is formed in a thin-walled circular-cylindrical shape, and the tip-covering portion 53 is hemispherical. The annular thin-walled portion 52 is interposed between the incremental portion 51 and the tip-covering portion 53, and the length of the annular thin-walled portion 52 in the longitudinal direction of the core 41 is shorter than the length of the incremental portion 51 in the same direction.

The outer diameter of the incremental portion 51 gradually increases from the small diameter end portion 511, which is the end on the cladding 42-side in the incremental portion 51, to the large diameter end portion 512, which is the end on the tip side of the core 41. The large diameter end portion 512 is the thickest part where the thickness of the incremental portion 51 is the thickest in the direction perpendicular to the central axis C of the core 41. The outer peripheral surface 51a of the incremental portion 51 is a tapered surface inclined to the central axis C of the core 41 without steps. Here, "step" refers to an annular stepped shape formed by a step change in the outer diameter of the light-scattering member 5.

The annular thin-walled portion 52 is formed thinner in thickness than the large diameter end portion 512 of the incremental portion 51. The annular thin-walled portion 52 is substantially constant in thickness and is formed so that the outer peripheral surface 52a is parallel to the central axis C of the core 41. A circularly stepped surface 51b is formed between the outer peripheral surface 51a of the incremental portion 51 and the outer peripheral surface 52a of the annular thin-walled portion 52.

Figures 4A, 4B:
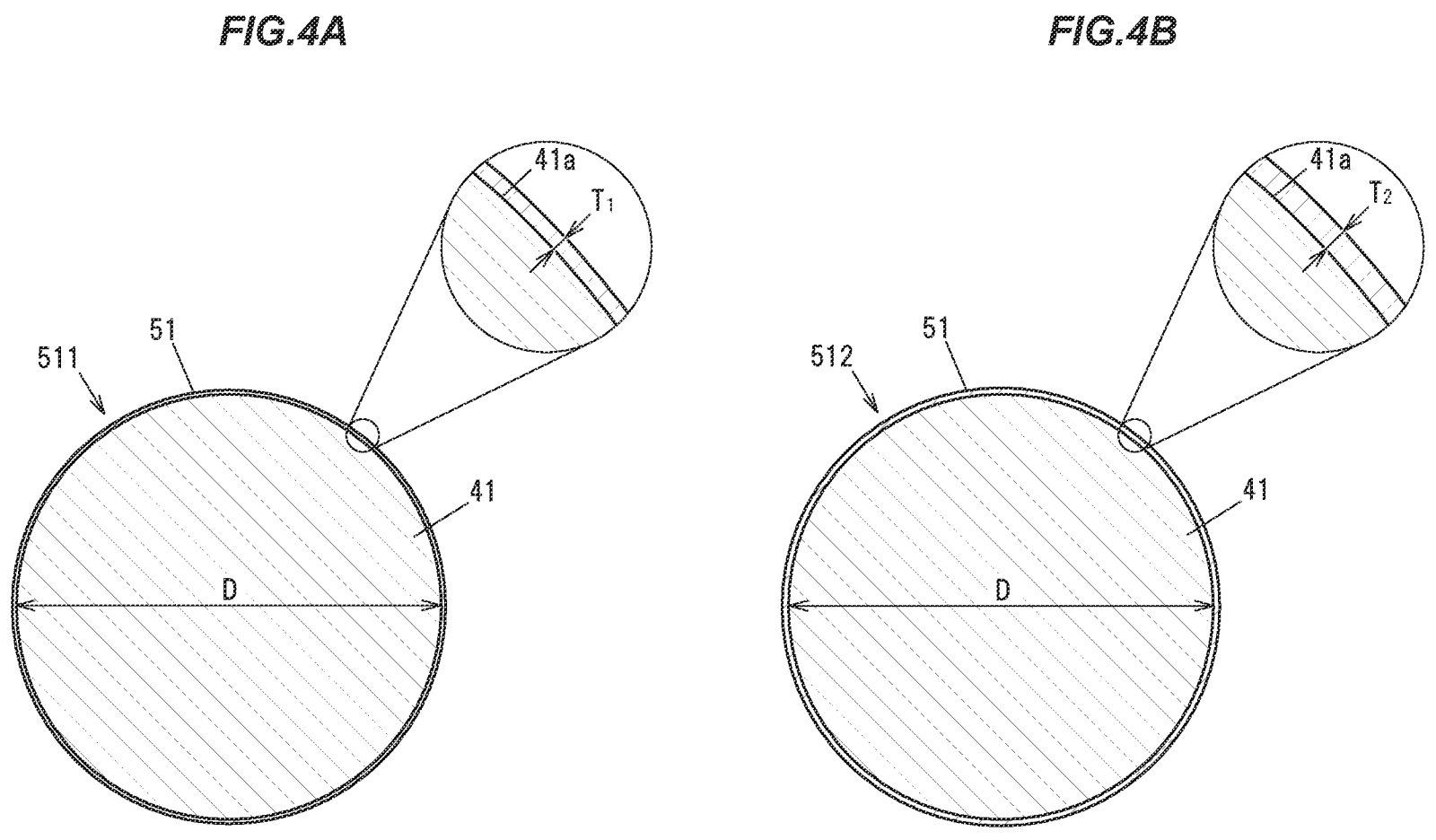

FIGS. 4A and 4B are cross-sectional views of the peripheral surface-emitting linear light guide 3 in a cross-section perpendicular to the central axis C of the core 41. FIG. 4A shows a cross-section of the small diameter end portion 511 of the incremental portion 51, and FIG. 4B shows a cross-section of the large diameter end portion 512 of the incremental portion 51.

The diameter D of the core 41 is, e.g., 200 μm. The thickness $T_1$ of the light-scattering member 5 at the small diameter end portion 511 is 2 μm as an example, while the thickness $T_2$ of the light-scattering member 5 at the large diameter end portion 512 is 3 μm as an example. The length L of the incremental portion 51 in the axial direction parallel to the central axis C of the core 41 (see FIG. 3B) is 55 mm as an example. In this case, the taper angle θ of the outer peripheral surface 51a of the incremental portion 51 is 0.001 degrees (=Tan$^{-1}$(0.001/55)). The thickness of the annular thin-walled portion 52 is, e.g., 0.5 μm.

In this embodiment, when the central axis C of the core 41 is straight, the angle (taper angle θ) of the outer peripheral surface 51a of the incremental portion 51 in a direction parallel to this central axis C is substantially constant, except for minute irregularities. However, the incremental portion 51 need not necessarily have a constant taper angle θ, as long as the thickness of the incremental portion 51 increases monotonically and gradually toward the tip side of the core 41.

Method for Manufacturing the Peripheral Surface-Emitting Linear Light Guide 3

Next, the manufacturing method of the peripheral surface-emitting linear light guide 3 will be described. The method for manufacturing the peripheral surface-emitting linear light guide 3 includes the following steps: an optical fiber-processing step of exposing the outer peripheral surface 41a of the core 41 from the cladding 42; a preparation step of preparing a liquid to serve as the light-scattering member 5; an immersion step of immersing a predetermined axial length range of the core 41 exposed from the cladding 42 into the liquid; and a pulling-up step of raising the core 41 and the liquid from the liquid by moving the core 41 and the liquid relative to each other in a vertical direction; and a curing step of curing the liquid adhered to the core 41.

The liquid prepared in the preparation step has a lower viscosity at higher temperatures. When the core 41 is immersed in the liquid in the immersion step and when the core 41 is pulled up in the pulling-up step, the temperature of the liquid is adjusted in such a manner that an appropriate amount of the liquid adheres to the core 41 depending on the viscosity of the liquid. The viscosity of the liquid may also be adjusted with an organic solvent (e.g., toluene, acetone) for dilution.

Figure 5A:
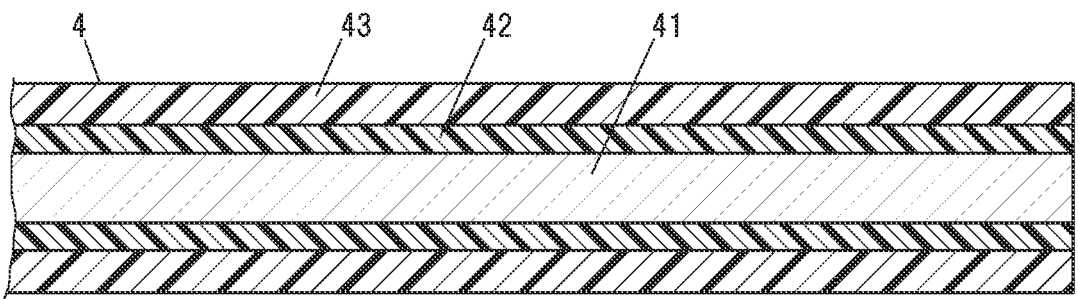
FIGS. 5A to 5C show cross-sectional views of the optical fiber processing steps.
Figure 5B:
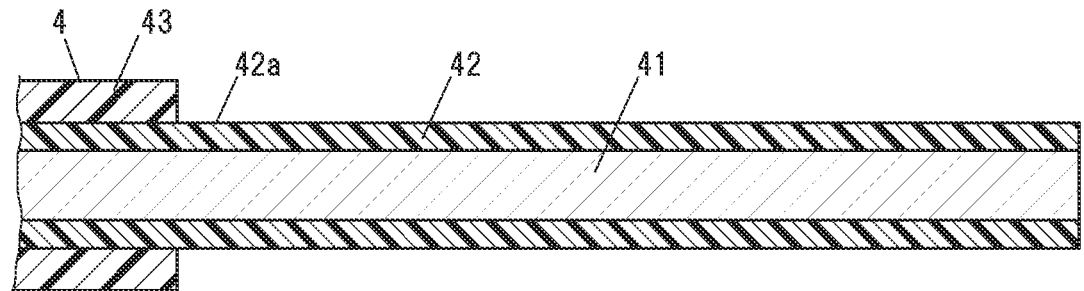
Figure 5C:
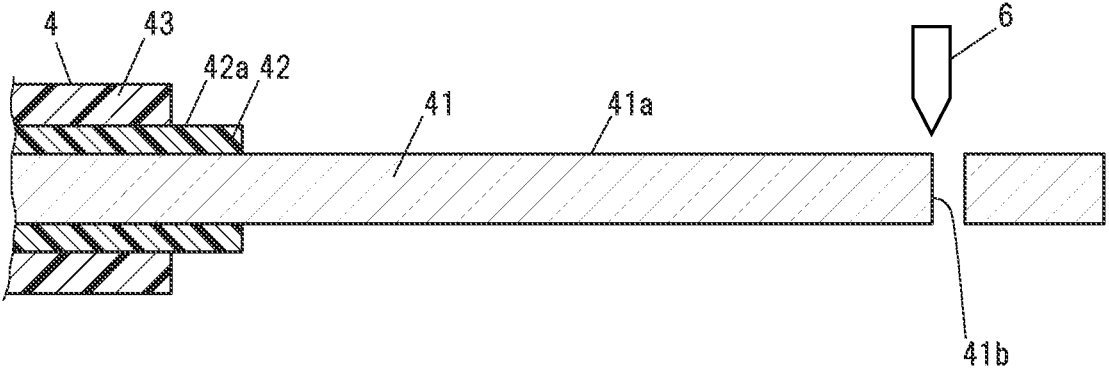

FIGS. 5A to 5C are cross-sectional views showing the optical fiber-processing step. In this step, an optical fiber 4 having a core 41, cladding 42, and sheath 43 is prepared as shown in FIG. 5A, and the sheath 43 is removed over a predetermined length range as shown in FIG. 5B. Then, as shown in FIG. 5C, the cladding 42 of the portion exposed from the sheath 43 is removed over a predetermined length range to expose the core 41 from the cladding 42, and a portion of the exposed core 41 is cut. The core 41 can be cut by, e.g., scratching a part of the core 41 using a cutting tool 6 and folding the core 41 at the scratched point. The tip surface 41b of the cut core 41 is a plane perpendicular to the longitudinal direction of the optical fiber 4.

Figure 6:
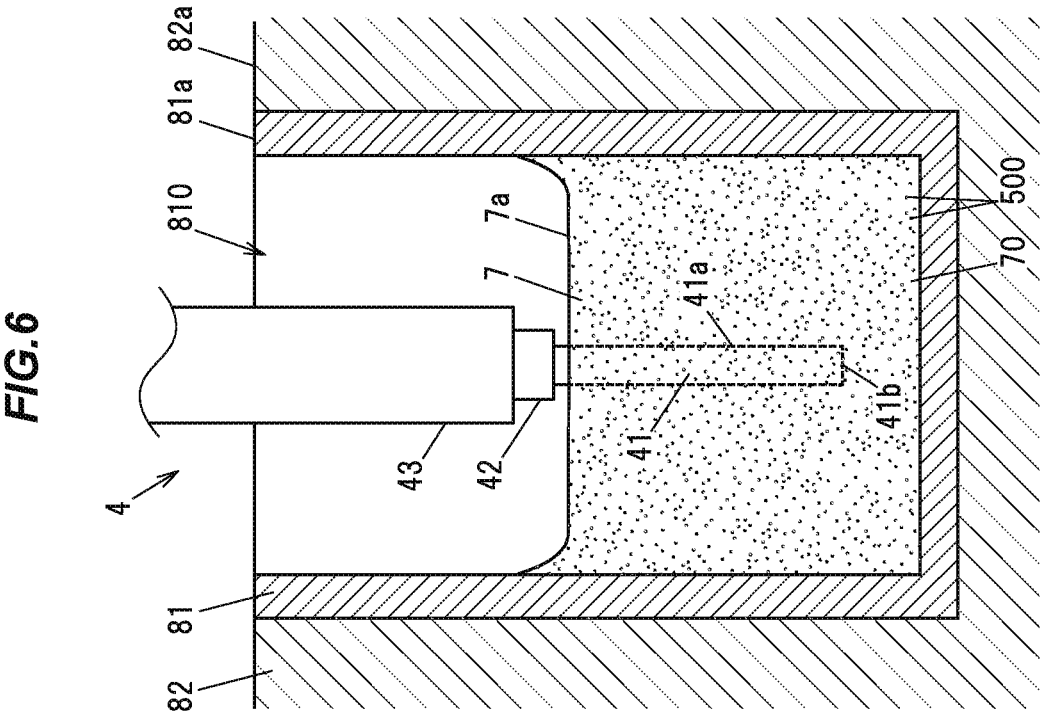
FIG. 6 is an explanatory diagram showing an immersion step.

FIG. 6 is an explanatory diagram showing the immersion step. In the immersion step, the core 41 is immersed in the liquid 7 prepared in the preparation step with the core 41 hanging vertically. The liquid 7 is a liquid base material 70, which is liquid at room temperature, in which the light-scattering particles 500 are dispersed and mixed. The liquid base material 70 is thermosetting and cured upon heating to become the solid base material 50. The liquid 7 is contained in a bottomed cylindrical syringe 81, and a heating jig 82 is arranged around the syringe 81. The heating jig 82 retains the liquid 7 at a predetermined temperature via the syringe 81 in such a manner that the liquid 7 has a viscosity suitable for the immersion and pulling-up steps. This predetermined temperature is, e.g., 40° C.

As shown in FIG. 6, the liquid surface 7a of the liquid 7 is lower than a top surface 81a of the syringe 81 and a top surface 82a of the heating jig 82, and the amount of liquid 7, the height of the syringe 81 and the height of the heating jig 82 should be adjusted in such a manner that the distance between the liquid surface 7a of the liquid 7 and the top surface 81a of the syringe 81 in the vertical direction is greater than the length of the core 41 in the portion exposed from the cladding 42. This means that the air in the space 810 in the syringe 81 that touches the liquid 7 is also heated by the heating jig 82, which prevents the liquid 7 from being cooled from the liquid surface 7a. The concentration of the light-scattering particles 500 in the liquid 7 is equivalent to the concentration of the light-scattering particles 500 in the light-scattering member 5. This concentration is, e.g., 1 mg/mL.

Figure 7:
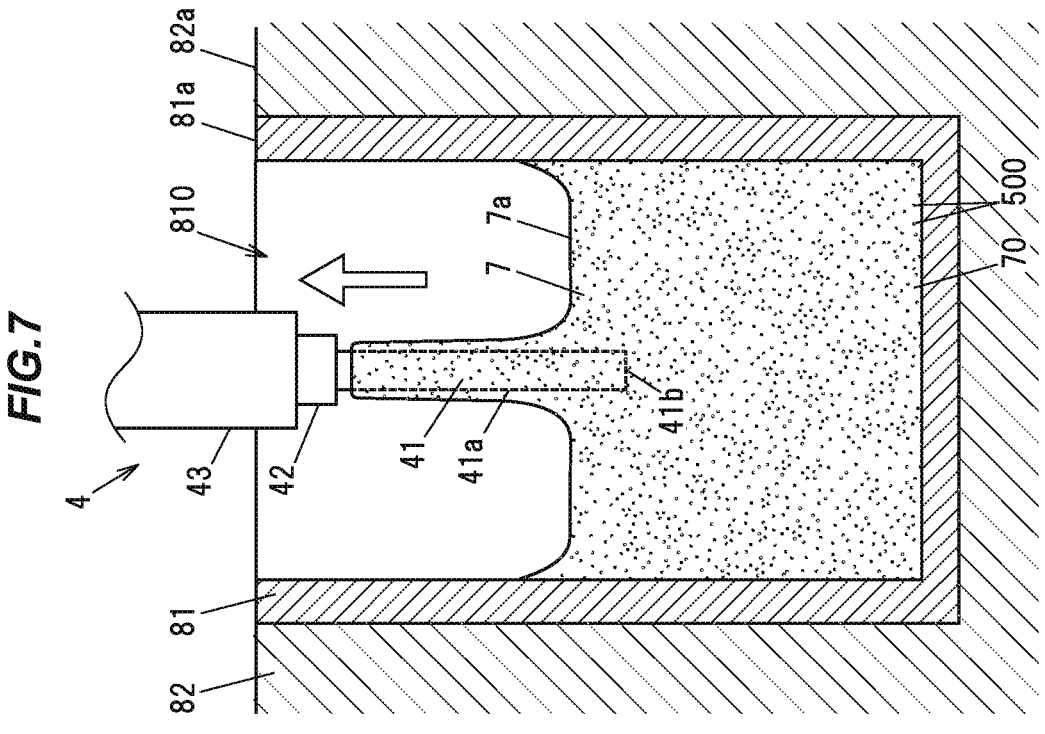
FIG. 7 is an explanatory diagram showing a pulling-up step.

FIG. 7 is an explanatory diagram of the pulling-up step. When forming the incremental portion 51 of the light-scattering member 5 in the pulling-up step, the pulling-up speed is varied to gradually increase the thickness of the liquid 7 adhering to the outer peripheral surface 41a of the core 41. The thickness of the adhered liquid 7 can be calculated by the following formula (1):

[Formula 1]

$$h = \frac{0.94(\eta U)^{2/3}}{\gamma^{1/6}\sqrt{\rho g}} \quad (1)$$

where the notations in the formula are h: thickness (m) of the liquid 7 adhering to the core 41, η: viscosity (Pa·s) of the liquid 7, U: pulling-up speed (m/s) of the core 41, γ: surface tension (mn/m) of the liquid 7, ρ: density (kg/m³) of the liquid 7, and g: gravitational acceleration (m/s²).

As is clear from the above formula (1), the thickness of the liquid 7 adhering to the core 41 varies with the pulling-up speed of the core 41, and the faster the pulling-up speed, the thicker the liquid 7 adhering to the core 41. In this method, the core 41 is immersed in the liquid 7 with the core 41 hanging vertically so that the tip surface 41b of the core 41 is vertically downward, and the core 41 is gradually pulled up, so the pulling-up speed is gradually increased when forming the incremental portion 51 of the light-scattering member 5 in the pulling-up step. When forming the annular thin-walled portion 52 and the tip-covering portion 53, the pulling-up speed is reduced and the core 41 is raised at a lower speed.

Figure 8A:
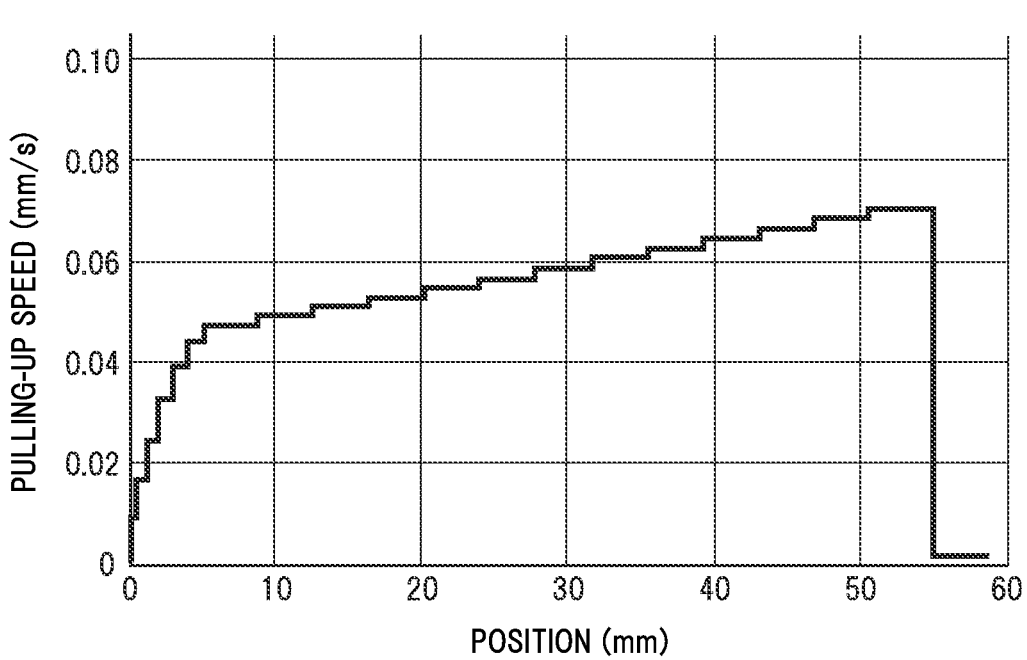
FIGS. 8A and 8B are graphs showing the results of measuring the relationship between the position of the core in the pulling step with the starting position of the core pulled up as the reference position, the pulling-up speed, and the thickness of the adhered liquid.
Figure 8B:
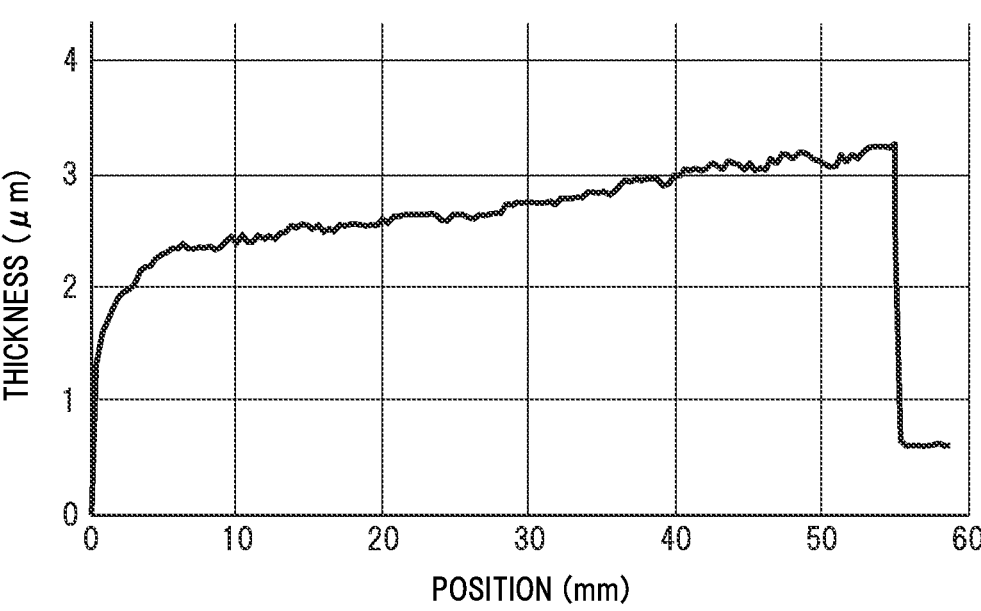

FIGS. 8A and 8B show the results of measuring the relationship between the position of the core 41, which is the reference position (0 mm) at the start of the pulling-up step, the pulling-up speed (mm/s), and the thickness (μm) of the adhered liquid 7. At the time of this measurement, the pulling-up speed was 0.05 mm/s when forming the small diameter end portion 511 of the incremental portion 51 and the pulling-up speed was 0.07 mm/s when forming the large diameter end portion 512, and the incremental portion 51 of the light-scattering member 5 was formed by gradually increasing the pulling-up speed from 0.05 mm/s to 0.07 mm/s. The light-scattering member 5 was formed by increasing the pulling speed gradually from 0.05 mm/s to 0.07 mm/s. In the pulling-up step, the pulling-up speed of core 41 was set at 0.002 mm/s at the 55 to 58 mm position to form the annular thin-walled portion 52. As shown in this graph, by varying the pulling-up speed of core 41, it is possible to control the thickness of the liquid 7 adhering to core 41 and thus the thickness of light-scattering member 5.

Figure 9:
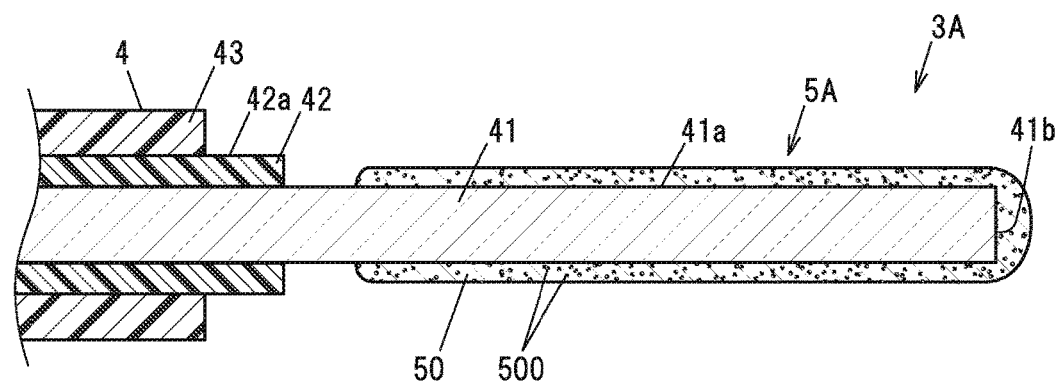
FIG. 9 is a cross-sectional view of a peripheral surface-emitting linear light guide according to a comparative example.

Configuration of a Peripheral Light-Emitting Linear Light Guide 3A in a Comparative Example FIG. 9 shows a cross-sectional view of a peripheral light-emitting linear light guide 3A in a comparative example. This peripheral surface-emitting linear light guide 3A, like the peripheral surface-emitting linear light guide 3 in the above embodiment, includes an optical fiber 4 in which outer peripheral surface 41a of the core 41 is exposed from the cladding 42, and the entire outer peripheral surface 41a of the core 41 is covered by a light-scattering member 5A over a predetermined axial length range. The configuration of the light-scattering member 5A is different from that of the light-scattering member 5 of the above embodiment.

In the peripheral surface-emitting linear light guide 3A in the comparative example, the thickness of the light-scattering member 5A covering the outer peripheral surface 41a of the core 41 is constant throughout the entire axial direction. The light-scattering member 5A has a number of light-scattering particles 500 dispersed and mixed in the base material 50 in the same concentration as in the above embodiment. The mixing ratio of the light-scattering particles 500 to the base material 50 in the light-scattering member 5A is homogeneous throughout the entire axial direction.

Figure 10:
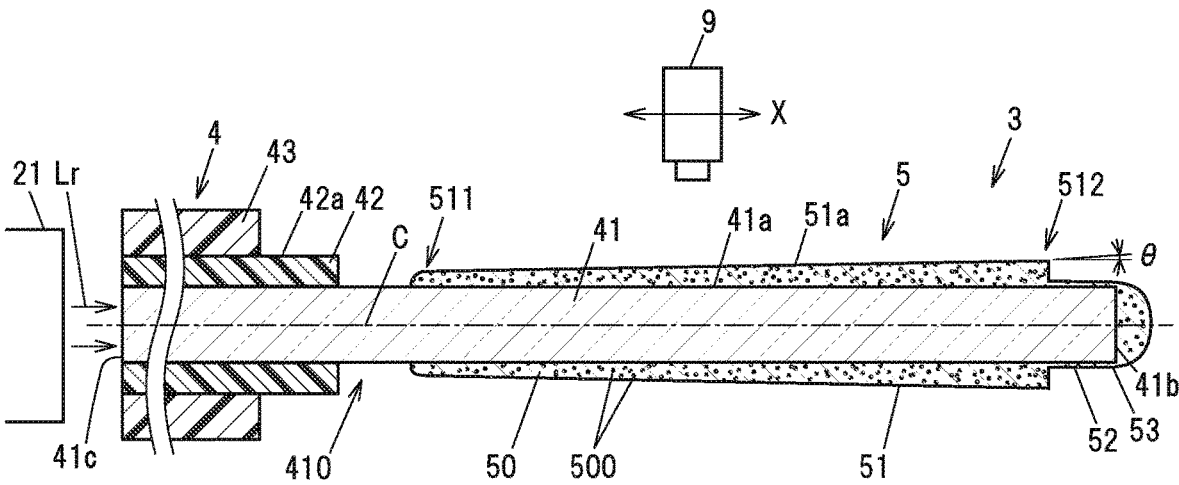
FIG. 10 is an explanatory diagram showing the measurement method for measuring the light intensity distribution in the axial direction of the outer peripheral surface-emitting linear light guide according to the embodiment and the outer peripheral surface-emitting linear light guide according to the comparative example.

Light Intensity Distribution of the Peripheral Surface-Emitting Linear Light Guide 3 According to the Embodiment and the Peripheral Surface-Emitting Linear Light Guide 3A According to the Comparative Example FIG. 10 is an explanatory diagram showing a measurement method for measuring the light intensity distribution in the axial direction of the peripheral surface-emitting linear light guide 3 according to the above-mentioned embodiment and the peripheral surface-emitting linear light guide 3A according to the comparative example. In FIG. 10, the state at the time of measurement of the peripheral surface-emitting linear light guide 3 is shown as an example, and the light intensity distribution is measured in the same way for the peripheral surface-emitting linear light guide 3A in the comparative example.

In this measurement method, the laser light Lr emitted by the light source 21 is incident on the incident surface 41c of the core 41, and the optical power meter 9, which measures the intensity of the light radiated from the light-scattering members 5, 5A in the radial direction of the core 41, is moved in the X direction parallel to the core 41 to measure the light intensity at multiple X direction positions.

Figure 11:
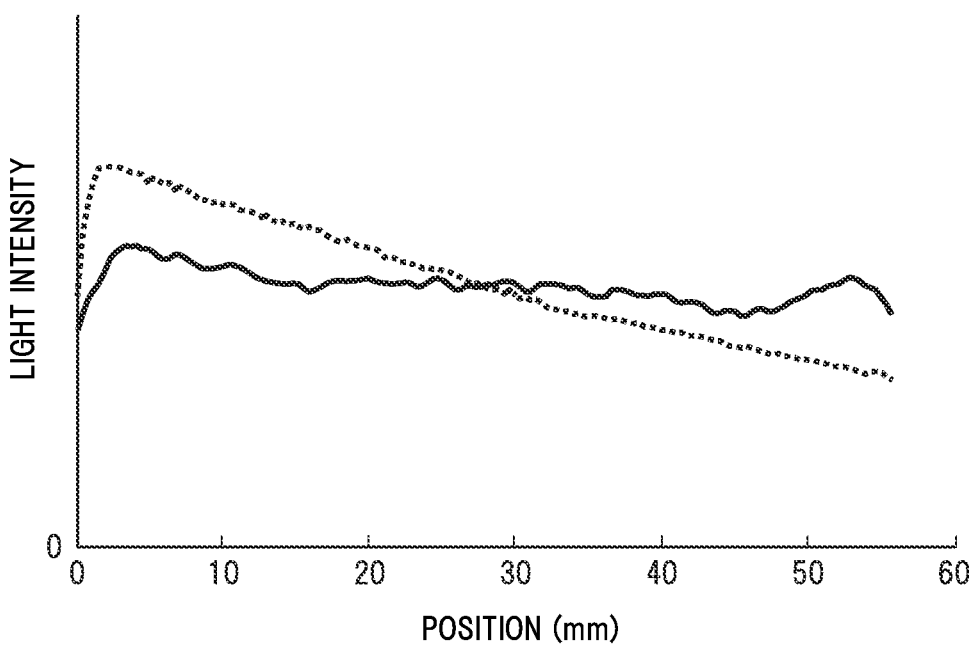
FIG. 11 is a graph showing the light intensity radiated in the radial direction of the core from the incremental portion of the light-scattering member of the outer peripheral surface-emitting linear light guide in the embodiment as a solid line, and the light intensity radiated in the radial direction of the core from the light-scattering member of the outer peripheral surface-emitting linear light guide in the comparative example as a broken line.

FIG. 11 is a graph showing the intensity of light radiated in the radial direction of the core 41 from the incremental portion 51 of the light-scattering member 5 of the peripheral surface-emitting linear light guide 3 of the above embodiment as a solid line, and the intensity of light radiated in the radial direction of the core 41 from the light-scattering member 5A of the peripheral surface-emitting linear light guide 3A of the comparative example as a broken line. The horizontal axis of this graph shows the position in the X-direction with the above reference position (the position of the end portion of the cladding 42-side of the light-scattering member 5, 5A) as 0. As shown in FIG. 11, the homogeneity of light intensity in the axial direction of the core 41 is enhanced in the peripheral surface-emitting linear light guide 3 according to the embodiment, compared to the peripheral surface-emitting linear light guide 3A according to the comparative example. This is due to the following reasons.

The light that is emitted from the core 41 and enters the light-scattering members 5, 5A, but does not hit the light-scattering particles 500 and is not scattered, is reflected at the outer peripheral surface of the light-scattering members 5, 5A (interface with the outside) and the outer peripheral surface of the core 41 (interface with the light-scattering members 5, 5A) while propagating within the base material 50. This is because the light coming from the light source 21 propagating through the core 41 has a shallow angle to the axial direction of the core 41. However, when the light incident on the light-scattering members 5, 5A hits the light-scattering particles 500, the light-scattering particles 500 reflect this light diffusely and the reflected light hits the outer peripheral surface of the light-scattering members 5, 5A at a relatively large angle. As a result, the light reflected by the light-scattering particles 500 is more likely to be radiated outward from the light-scattering members 5, 5A.

In the peripheral surface-emitting linear light guide 3A of the comparative example, the thickness of the light-scattering member 5A and the mixing ratio of the light-scattering particles 500 are homogeneous throughout the entire axial direction. The light in the core 41 gradually becomes weaker due to dissipation to the outside as it approaches the tip side, and the light incident on the light-scattering member 5A also gradually becomes weaker. Therefore, the intensity of light radiated from the light-scattering member 5A also gradually decreases toward the tip side of the core 41. In other words, in the peripheral surface-emitting linear light guide 3A, the light intensity distribution is such that the light intensity gradually decreases toward the tip side of the core 41.

On the other hand, in the peripheral surface-emitting linear light guide 3, the thickness of the incremental portion 51, which is the essential portion of the light-scattering member 5, increases gradually toward the tip side of the core 41, so that light incident on the light-scattering member 5 easily returns to the core 41 near the small diameter end portion 511, and the light incident on the light-scattering member 5 is easily radiated outward near the large diameter end portion 512. In other words, in the peripheral surface-emitting linear light guide 3, a balance between the intensity of light in the core 41 and the case of radiation to the outside of the light-scattering member 5 results in a flat overall light intensity distribution.

In the peripheral surface-emitting linear light guide 3, the annular thin-walled portion 52 is formed by slowly pulling the core 41 away from the liquid surface 7a of the liquid 7 by decreasing the pulling speed near the tip portion of the core 41 in the pulling-up step. This prevents a large amount of liquid 7 from adhering to the periphery of the tip surface 41b of the core 41 and forming a large hemispherical resin ball due to surface tension. If a large resin ball is formed on the tip surface 41b of the core 41, this resin ball will contain a large amount of light-scattering particles 500. If this is the case, the light intensity may become locally stronger at the resin ball, and the homogeneity of the light intensity distribution may be reduced. In other words, the annular thin-walled portion 52 has the function of suppressing the decrease in homogencity of light intensity.

A reflective film made of a metal with high reflectivity, such as gold or silver, may be formed on the tip surface 41b of the core 41, e.g., by sputtering. A black paint may also be applied to the tip surface 41b of the core 41. In this case, the annular thin-walled portion 52 and the tip-covering portion 53 may not be formed on the light-scattering member 5. In other words, the light-scattering member 5 need only have at least one portion in the longitudinal direction of the core 41 as the incremental portion 51.

Figure 12:
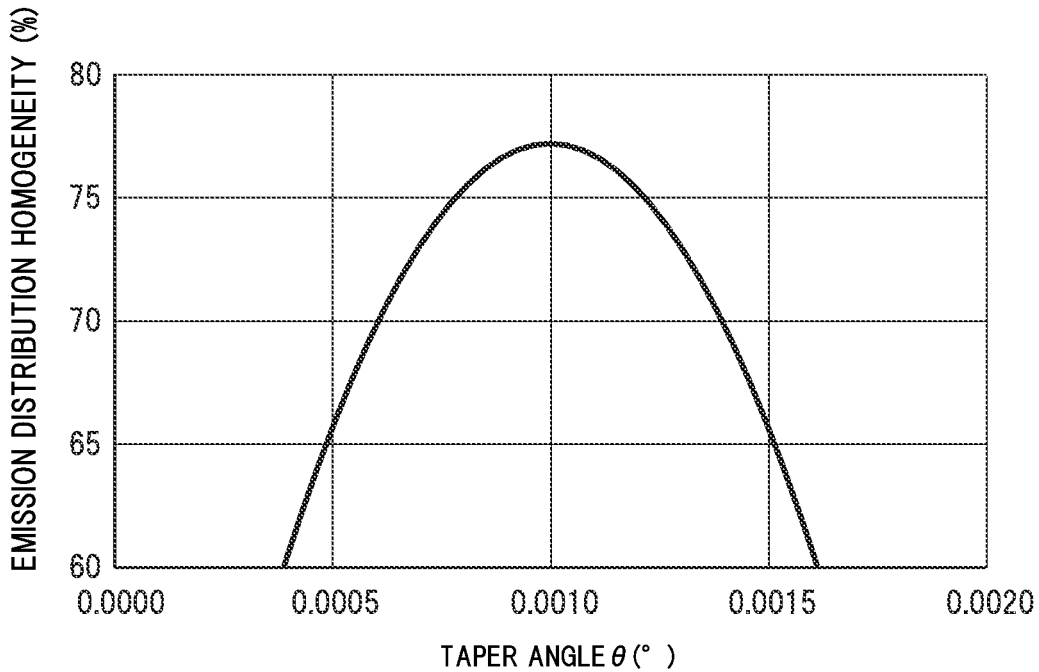
FIG. 12 is a graph showing an example of the results of calculating the homogeneity of emission distribution by changing the taper angle of the outer peripheral surface of the incremental portion of the light-scattering member.

FIG. 12 shows an example of the results of calculating the homogeneity of emission distribution, which is an index value indicating the homogeneity of the intensity of light radiated in the radial direction of the core 41 from the outer peripheral surface 51a between the small diameter end portion 511 and the large diameter end portion 512 of the incremental portion 51, by changing the taper angle θ of the outer peripheral surface 51a of the incremental portion 51 by increasing or decreasing the thickness of the large diameter end portion 512 of the incremental portion 51. Here, the homogencity of emission distribution (i.e., the emission distribution homogeneity) (%) is a value obtained by multiplying the quotient obtained by dividing the minimum value of light intensity measured by an optical power meter 9 by the maximum value in the measurement method shown in FIG. 10 by 100. For example, if a liquid 7 with a concentration of light-scattering particles 500 of 1 mg/mL is used and the target value of homogeneity of emission distribution is set at 70% or more, this target can be achieved within a taper angle θ of 0.0006 degrees or more and 0.0014 degrees or less. For example, if the target value of emission distribution homogeneity is set at 75% or more, this target can be achieved within a taper angle θ of 0.0008 degrees or more and 0.0012 degrees or less.

Functions and Effects of the Embodiment

According to the embodiment described above, it is possible to increase the homogeneity of the intensity of the light radiated from the light-scattering member 5A compared to the case where the thickness of the light-scattering member 5A is constant, as in the case of the peripheral surface-emitting linear light guide 3A in the comparative example. In addition, by adjusting the pulling-up speed of the core 41 in the pulling-up step, it is possible to form the incremental portion 51 whose thickness gradually increases toward the tip side of the core 41 in a single raising, thus enabling lower cost compared to the method of forming a light-scattering member having multiple layers with different light-scattering particle mixing ratios.

SUMMARY OF THE EMBODIMENTS

Next, the technical concepts that can be grasped from the above-described embodiment will be described with the aid of the codes, etc. in the embodiment. However, each code in the following description does not limit the members in the scope of claims to the parts, etc. specifically shown in the embodiment.

According to the first feature, a peripheral surface-emitting linear light guide 3 having an optical fiber 4 including a core 41, an outer peripheral surface 41a of which is exposed from a cladding 42 at one end in a longitudinal direction, and a light-scattering member 5, which covers an entire periphery of the outer peripheral surface 41a of the core 41 in an exposed portion over a predetermined axial length range. The light emitted from the outer peripheral surface 41a of the core 41 is scattered and radiated by the light-scattering member 5. The light-scattering member 5 has a light transmissive base material 50 having a higher refractive index than the core 41 and light-scattering particles 500 that scatter the light incident on the base material 50. The light-scattering particles 500 are dispersed and mixed in a certain proportion throughout the base material 50. At least a portion of the light-scattering member 5 in the longitudinal direction is an incremental portion 51 whose thickness increases gradually toward a tip side of the core 41.

According to the second feature, in the peripheral surface-emitting linear light guide 3 as described in the first feature, the outer peripheral surface 51a of the incremental portion 51 is a tapered surface inclined to a central axis C of the core 41 without steps.

According to the third feature, in the peripheral surface-emitting linear light guide 3 described in the first feature, the light-scattering member 3 has, on the tip side of the core 41 from the incremental portion 51, an annular thin-walled portion 52 which is thinner than a thickest portion (large diameter end portion) 512 of the incremental portion 51.

According to the fourth feature, a method for manufacturing the peripheral surface-emitting linear light guide 3 according to any one of the first to third features, includes an optical fiber-processing step of exposing the outer peripheral surface 41a of the core 41 from the cladding 42; a preparation step of preparing a liquid 7 to be used as the light-scattering member 5; an immersion step of immersing the exposed core 41 in the liquid 7; a pulling-up step of pulling-up the core 41 from the liquid 7 by moving the core 41 and the liquid 7 relative to each other in a vertical direction; and a curing step of curing the liquid 7 adhered to the core 41. In the pulling-up step, when forming the incremental portion 51 of the light-scattering member 5, a pulling-up speed is varied to gradually increase a thickness of the liquid 7 adhering to the outer peripheral surface 41*a* of the core 41.

The above-described embodiments of the invention are not limiting the invention as claimed in the claims. It should also be noted that not all of the combinations of features described in the embodiment are essential to the solution of the technical problem of the invention.

The invention claimed is:

1. A peripheral surface-emitting linear light guide, comprising:

an optical fiber including a core, an outer peripheral surface of which is exposed from a cladding at one end in a longitudinal direction; and a light-scattering member that covers an entire periphery of the outer peripheral surface of the core in an exposed portion over a predetermined axial length range, wherein light emitted from the outer peripheral surface of the core is scattered and radiated by the light-scattering member, wherein the light-scattering member comprises a light transmissive base material having a higher refractive index than the core and light-scattering particles that scatter the light incident on the base material, and the light-scattering particles are dispersed and mixed in a certain proportion throughout the base material, wherein at least a portion of the light-scattering member in the longitudinal direction is an incremental portion whose thickness increases gradually toward a tip side of the core, and wherein the outer peripheral surface of the incremental portion is a tapered surface inclined to a central axis of the core without steps.

2. A method for manufacturing the peripheral surface-emitting linear light guide according to claim 1, comprising:

processing the optical fiber to expose the outer peripheral surface of the core from the cladding;

preparing a liquid to be used as the light-scattering member;

immersing the exposed core in the liquid;

pulling-up the core from the liquid by moving the core and the liquid relative to each other in a vertical direction; and curing the liquid adhered to the core, wherein, in the pulling-up step, when forming the incremental portion of the light-scattering member, a pulling-up speed is varied to gradually increase a thickness of the liquid adhering to the outer peripheral surface of the core.

3. The peripheral surface-emitting linear light guide according to claim 1, wherein the incremental portion has a taper angle θ with respect to the central axis of the core, and wherein $0.0006° \leq \theta \leq 0.0014°$.

4. The peripheral surface-emitting linear light guide according to claim 1, wherein the light-scattering member further comprises, on the tip side of the core relative to the incremental portion, an annular thin-walled portion that is thinner than a thickest portion of the incremental portion.

5. The peripheral surface-emitting linear light guide according to claim 4, wherein an outer peripheral surface of the annular thin-walled portion is parallel to the central axis of the core.

6. The peripheral surface-emitting linear light guide according to claim 4, wherein the light-scattering member further comprises a tip-covering portion that covers a distal end face of the core.

7. The peripheral surface-emitting linear light guide according to claim 1, wherein the light-scattering particles are selected from the group consisting of titanium oxide, aluminum oxide, silver, copper, iron, and alloys thereof.

8. The peripheral surface-emitting linear light guide according to claim 1, wherein the light-scattering particles comprise titanium oxide ($TiO_2$).

9. The peripheral surface-emitting linear light guide according to claim 1, wherein the light transmissive base material comprises a silicone resin.

10. The peripheral surface-emitting linear light guide according to claim 1, wherein a refractive index of the light transmissive base material is at least 1.50 and a refractive index of the core is 1.46.

11. The peripheral surface-emitting linear light guide according to claim 1, wherein the core is made of a quartz glass and the cladding is made of a polymer cladding.

12. The peripheral surface-emitting linear light guide according to claim 1, wherein the exposed portion of the core covered by the light-scattering member has an axial length of 3 cm to 7 cm.

13. The peripheral surface-emitting linear light guide according to claim 1, wherein a mixing ratio of the light-scattering particles to the base material in the light-scattering member is homogeneous throughout the entire longitudinal direction.

14. A peripheral surface-emitting linear light guide, comprising:

an optical fiber including a core, an outer peripheral surface of which is exposed from a cladding at one end in a longitudinal direction; and a light-scattering member that covers an entire periphery of the outer peripheral surface of the core in an exposed portion over a predetermined axial length range, wherein light emitted from the outer peripheral surface of the core is scattered and radiated by the light-scattering member, wherein the light-scattering member comprises a light transmissive base material having a higher refractive index than the core and light-scattering particles that scatter the light incident on the base material, and the light-scattering particles are dispersed and mixed in a certain proportion throughout the base material, wherein at least a portion of the light-scattering member in the longitudinal direction is an incremental portion whose thickness increases gradually toward a tip side of the core, and wherein the light-scattering member further comprises, on the tip side of the core from the incremental portion, an annular thin-walled portion which is thinner than a thickest portion of the incremental portion.

15. A method for manufacturing the peripheral surface-emitting linear light guide according to claim 14, comprising:

processing the optical fiber to expose the outer peripheral surface of the core from the cladding;

preparing a liquid to be used as the light-scattering member;

immersing the exposed core in the liquid;

pulling-up the core from the liquid by moving the core and the liquid relative to each other in a vertical direction; and curing the liquid adhered to the core,

wherein, in the pulling-up step, when forming the incremental portion of the light-scattering member, a pulling-up speed is varied to gradually increase a thickness of the liquid adhering to the outer peripheral surface of the core.

16. The peripheral surface-emitting linear light guide according to claim 14, wherein the incremental portion has a taper angle θ with respect to the central axis of the core, and wherein $0.0006° \leq \theta \leq 0.0014°$.

17. The peripheral surface-emitting linear light guide according to claim 14, wherein the core is made of a quartz glass and the cladding is made of a polymer cladding.

18. The peripheral surface-emitting linear light guide according to claim 14, wherein the exposed portion of the core covered by the light-scattering member has an axial length of 3 cm to 7 cm.

19. The peripheral surface-emitting linear light guide according to claim 14, wherein a mixing ratio of the light-scattering particles to the base material in the light-scattering member is homogeneous throughout the entire longitudinal direction.

* * * * *